United States Patent
Frostell et al.

(10) Patent No.: US 9,895,234 B2
(45) Date of Patent: Feb. 20, 2018

(54) SPINAL CORD DEVICES AND METHODS FOR PROMOTING AXONAL REGENERATION

(71) Applicant: BioArctic Neuroscience AB, Stockholm (SE)

(72) Inventors: Arvid Frostell, Stockholm (SE); Per Mattsson, Täby (SE); Mikael Svensson, Stockholm (SE)

(73) Assignee: BIOARCTIC NEUROSCIENCE AB, Stockholm (SE)

( * ) Notice: Subject to any disclaimer, the term of this patent is extended or adjusted under 35 U.S.C. 154(b) by 807 days.

(21) Appl. No.: 14/361,650

(22) PCT Filed: Dec. 3, 2012

(86) PCT No.: PCT/IB2012/056924
§ 371 (c)(1),
(2) Date: May 29, 2014

(87) PCT Pub. No.: WO2013/084137
PCT Pub. Date: Jun. 13, 2013

(65) Prior Publication Data
US 2015/0088257 A1    Mar. 26, 2015

Related U.S. Application Data (60) Provisional application No. 61/567,450, filed on Dec. 6, 2011.

(51) Int. Cl.
*A23F 5/04* (2006.01)
*A61B 17/11* (2006.01)
(Continued)

(52) U.S. Cl.
CPC ........ *A61F 2/4455* (2013.01); *A61B 17/1128* (2013.01); *A61F 2/30771* (2013.01);
(Continued)

(58) Field of Classification Search
CPC ......... A61B 17/1128; A61B 2017/1132; A61F 2/4455; A61F 2/30771; A61F 2/4657; A61L 27/50; A61L 27/54
(Continued)

(56) References Cited

U.S. PATENT DOCUMENTS 5,735,863 A * 4/1998 Della Valle ........... A61L 31/042
                                                                  606/152
6,214,021 B1    4/2001   Hadlock et al.
(Continued)

FOREIGN PATENT DOCUMENTS

WO       98/04197 A1     2/1998
WO    2007/111562 A1    10/2007

OTHER PUBLICATIONS

Official Action from corresponding European Application No. 12815796.3, dated Jun. 7, 2016.
(Continued)

*Primary Examiner* — Katrina Stransky
*Assistant Examiner* — Marie C Black
(74) *Attorney, Agent, or Firm* — Porter Wright Morris & Arthur LLP (57) ABSTRACT

A spinal cord device comprises a body formed of a biocompatible, biodegradable matrix. The body includes proximal, cranial and distal, caudal surfaces for connection to two ends of an injured spinal cord after removal of an injured section and has through channels with openings in the cranial and caudal surfaces for connection of descending motor pathways and ascending sensory pathways. The device has a transversal diameter ($D_t$), an anteroposterior diameter ($D_a$) and a length (L), wherein $D_t$ is from 9 to 13 mm and the ratio anteroposterior diameter/transverse diameter (RAPT) is from 0.5 to 1.0 and wherein the position and dimension of the channels, RAPT value, and cranial surface area and/or
(Continued)

caudal surface area of the device are adopted to the shape, level, dimension of white and gray matter, and size of the injured spinal cord for optimal connection between spinal cord tracts. Kits and methods employ such devices.

7 Claims, 3 Drawing Sheets (51) Int. Cl.
    *A61F 2/46*     (2006.01)
    *A61L 27/50*     (2006.01)
    *A61L 27/54*     (2006.01)
    *A61L 27/58*     (2006.01)
    *A61B 17/00*     (2006.01)
    *A61F 2/30*     (2006.01)
    *A61F 2/44*     (2006.01)

(52) U.S. Cl.
    CPC ............ *A61F 2/4657* (2013.01); *A61L 27/50* (2013.01); *A61L 27/54* (2013.01); *A61L 27/58* (2013.01); *A61B 2017/00004* (2013.01); *A61F 2002/30616* (2013.01); *A61F 2002/30772* (2013.01); *A61F 2002/4659* (2013.01); *A61F 2310/0097* (2013.01); *A61F 2310/00976* (2013.01); *A61L 2430/32* (2013.01); *A61L 2430/38* (2013.01)

(58) Field of Classification Search
    USPC .................................. 606/152, 153, 154, 155
    See application file for complete search history.

(56) References Cited

U.S. PATENT DOCUMENTS

| | | |
|---|---|---|
| 6,235,041 B1 | 5/2001 | Cheng et al. |
| 2004/0102793 A1 | 5/2004 | Yaszemski et al. |
| 2004/0199186 A1 | 10/2004 | Kuffler et al. |
| 2009/0169596 A1* | 7/2009 | Svensson ............ A61B 17/1128 424/423 |
| 2010/0076465 A1* | 3/2010 | Wiberg .............. A61B 17/1128 606/152 |
| 2011/0276066 A1* | 11/2011 | Pandit .................... A61L 27/24 606/152 |
| 2015/0037436 A1* | 2/2015 | Huang ................... A61K 35/35 424/574 |

OTHER PUBLICATIONS

Official Action from corresponding Chinese Application No. 2012800691719, dated Feb. 23, 2016, and English translation.
Search Report from corresponding Chinese Application No. 2012800691719, dated Feb. 23, 2016, and English translation.
Fraidakis et al, Experimental Neurology, 188:33-42 (2004).
Cordeiro et al, Plastic and Reconstructive Surgery, 83(6):1013-1021.

* cited by examiner

SPINAL CORD DEVICES AND METHODS FOR PROMOTING AXONAL REGENERATION

FIELD OF THE INVENTION

The present invention relates to treatment of Spinal Cord Injury (SCI) and is directed to biodegradable devices having dimensions adopted to the shape, level, size and dimensions of white and gray matter of the injured spinal cord. These devices are to be surgically inserted at the site of injury for promotion of axon regeneration and outgrowth for bridging a gap in the spinal cord. The devices are designed to provide motor as well as sensory connections from white to gray matter between two spinal cord ends. The invention is also directed to kits comprising a range of devices, methods for selecting an optimal device for a specific patient, and surgical methods for implantation of a device according to the invention.

BACKGROUND OF THE INVENTION

A spinal cord injury occurs when trauma or disease damages the spinal cord and results in partial or complete paralysis. The level of paralysis is determined by where the damage occurs, i.e. in the neck or in the back. Besides paralysis there are usually signs of sensory loss, incontinence, intractable pain and pressure sores. The world-wide annual incidence of SCI has been estimated to be around 22 per million with approximately 2.5 million survivors living with SCI induced paralysis. As today, there is no therapy which restores or even significantly improves the spinal cord function in those severe cases.

Attempts to use peripheral nerve grafts for bridging spinal cord gaps in rats was reported by Cheng et al in 1996 (Science, 273: 510). The nerve grafts redirected descending motor pathways from cranial (proximal) non-permissive white matter to caudal (distal) permissive gray matter and ascending pathways from caudal white to cranial gray matter. FGF1 was added to decrease gliosis and enhance axon regeneration. The nerve grafts were positioned in the gap between the two spinal cord ends and kept in the right position by tissue glue. Animals subjected to the repair procedure, i.e. implantation of nerve grafts together with FGF1, significantly improved in their hind limb function. The first improvements were observed a few weeks after surgery and continued through one year of observation. Attempts to further improve the spinal cord repair procedures have been made by using magnetic resonance imaging (MRI) to assess the lesion extent before surgery, see Fraidakis et al (Experimental Neurology 188(2004)33-42). Thin serial MRI sections allowed identification of gray and white matter and visualization of cyst formation. After resecting the lesioned spinal cord, as necessary, autologous intercostal nerve grafts were implanted and the repair site was embedded in fibrin glue containing acidic FGF.

Preformed devices for bridging a gap in a spinal cord and methods for manufacture thereof, are also known from prior art, see e.g. U.S. Pat. No. 6,235,041 (Cheng and Olsson), U.S. Pat. No. 7,163,545 (Yaszemski et al) and WO 2007/111562 (Svensson and Mattsson). General designs are disclosed, but there is no teaching of devices adopted for the level, size and shape of the spinal cord injury.

However, in spite of considerable time from early disclosures of the basic principle of connecting the routing of tracts in white to gray matter, the translation into a clinically applicable method has been absent. Still, no product is available on the market. The spinal cord is an extremely important part of the central nervous system, where a patient with a complete injury faces a permanent loss of function below the site of injury, with devastating consequences for the patient's quality of life, as well as long-term costs to finance the assistance to the patient. In many cases the patient is a fairly young person who has been involved in a serious accident and will have to spend the rest of life with no chance for functional improvements.

SUMMARY OF THE INVENTION

Accordingly, it is an object of the present invention to provide improved devices, kits and methods for treatment of Spinal Cord Injury (SCI) and, more specifically, for bridging an injured spinal cord and promoting axonal regeneration.

In a first embodiment, the invention is directed to a spinal cord device for bridging an injured spinal cord and promoting axonal regeneration, the spinal cord device comprising a body formed of a biocompatible, biodegradable matrix. The body includes a proximal, cranial surface and a distal, caudal surface for connection to two ends of an injured spinal cord after removal of an injured spinal cord section, and has through channels with openings in the cranial surface and the caudal surface for connection of descending motor pathways from cranial white to caudal gray matter and ascending sensory pathways from caudal white to cranial gray matter of the two spinal cord ends. The spinal cord device has a transversal diameter ($D_t$), an anteroposterior diameter ($D_a$) and a length (L). wherein $D_t$ is within a range of from 9 to 13 mm and the ratio anteroposterior diameter/transverse diameter (RAPT) is in a range of from 0.5 to 1.0 and wherein the position and dimension of the channels, the RAPT value, and the cranial surface area and/or the caudal surface area of the device are adopted to the shape, level, dimension of white and gray matter, and size of the injured spinal cord for optimal connection between spinal cord tracts.

In another embodiment, the invention is directed to spinal cord device kit comprising a plurality of devices for bridging an injured spinal cord and promoting axonal regeneration, each device comprising a body formed of a biocompatible, biodegradable matrix with a proximal, cranial surface and a distal, caudal surface for connection to two ends of an injured spinal cord after removal of an injured spinal cord section, the body having through channels with openings in the cranial surface and the caudal surface for connection of descending motor pathways from cranial white to caudal gray matter and ascending sensory pathways from caudal white to cranial gray matter of the two spinal cord ends. Each device of the kit has a transversal diameter ($D_t$), an anteroposterior diameter ($D_a$) and a length (L), wherein the respective $D_t$'s of the respective devices in the kit are mainly evenly distributed within a range of from 9 to 13 mm and the respective ratio anteroposterior diameter/transverse diameter (RAPT)s of the respective devices in the kit are in a range of from 0.5 to 1.0 and wherein the position and dimension of the channels, the specific RAPT value and the cranial and/or caudal surface areas of each device are adopted to a shape, level, dimension of white and gray matter, and size of an injured spinal cord for optimal connection between spinal cord tracts.

In a further embodiment, the invention is directed to method for restoring or at least substantially restoring an injured spinal cord of a patient, comprising the steps of i) determining the cross-section surface area and the anteroposterior diameter ($D_a$)/transverse diameter ($D_t$) ratio (RAPT) of an injured section of the spinal cord after resection of the nerve ends as necessary to reach healthy spinal cord tissue, ii) selecting a spinal cord device according to the invention having the ratio anteroposterior/transverse diameter (RAPT) determined in i) and a slightly larger surface area than the spinal cord cross-section surface area to fit the dimensions of said injured section for optimal connection between the spinal cord tracts, iii) optionally soaking the device in a solution comprising one or more pharmaceutically active substances, iv) positioning peripheral autologous nerves in the through channels, and v) implanting the device to bridge the gap in the injured spinal cord or nerve.

The devices, kits and methods provide for improvements in the treatment of spinal cord injuries. Various embodiments and these and additional advantages will be more fully described in the following detailed description.

BRIEF DESCRIPTION OF THE DRAWINGS

The following detailed description will be more fully understood in view of the Drawings, in which.

The Drawings are discussed in further detail in the detailed description and are non-limiting of the invention as described.

DETAILED DESCRIPTION

The devices, kits and methods of the present invention further improve the technique for repair of a permanently injured spinal cord by providing devices which are adopted to the neuronal level and the dimensions, the more or less ellipsoidal cross section of the spinal cord at the injury site, as well as the length of the gap, after the spinal cord ends have been resected as required. Along a longitudinal section of the spinal cord, the amount of white tissue decreases successively from the cranial end to the caudal end and combined with the varying degree of ellipsoidal shape, this requires that the channel system of the device is adopted accordingly. While not wishing to be bound by theory, the present inventors believe that one reason for the lack of viable products available for treating spinal cord injury is the fact that there has not been any device available which takes these various parameters into consideration and provides a tool for optimized regeneration of the complicated functional anatomy of the spinal cord. Precision and safety are key factors to be optimized.

Various embodiments of the invention will in the following be discussed and exemplified from the thoracic part of the spinal cord, i.e. the T2-T12 level.

Figure 1:
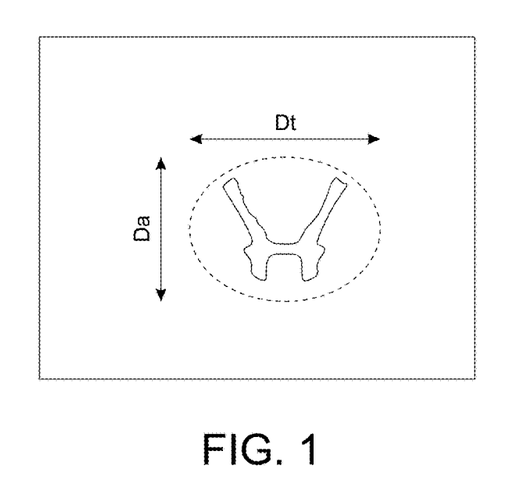
FIG. 1 shows a schematic cross section of a spinal cord, where the "H"-shape represents gray matter and is surrounded by white matter.

The cross section of the human spinal cord at different levels is approximated to an elliptical shape, where the wider diameter is referred to as the transverse diameter, $D_t$ and the narrower is referred to as the anteroposterior diameter, $D_a$ (see FIG. 1). As shown in FIG. 1, the cross section of a spinal cord includes an "H"-shape of gray matter and is surrounded by white matter.

There is evidence that a regeneration strategy requires healthy and functional spinal cord tissue at both interfaces with the device for efficient regeneration. In other words, if a substrate for regeneration was brought into contact with scar tissue in the injury zone, no regeneration would occur. The golden standard for determining the extent of a spinal cord injury at present is Magnetic Resonance Imaging (MRI). Unfortunately, MRI is unable to directly measure function of that spinal cord tissue. Functional evaluation of the spinal cord can be done with neurophysiology, but prior use of the technique has been restricted to evaluation of the cranial border of function in a SCI-patient. In any regeneration strategy aiming at bridging a spinal cord gap, preoperative determination of the caudal border of SCI is essential, because it makes it possible to calculate the expected regeneration distance required to reach healthy tissue. To overcome this problem, a recently developed non-invasive protocol combining MRI and neurophysiology has been described (Frostell et al, Spinal Cord, (2012) 50:315-319) to determine both the functional and anatomical extent of the lesion in SCI-patients.

Briefly, electromyograms are acquired from muscles innervated by spinal cord segments above the lesion (injury), at the lesion and under the lesion. All muscles are examined both during voluntary activation as well as activation of a patient's spasticity in the paretic part of the body. This yields three distinct patterns of motor unit potentials (MUP): above the lesion normal MUPs are found during voluntary activation and no MUPs during activation of spasticity. At the level of neurological loss, no MUPs are seen and evidence of chronic denervation indicated by positive sharp waves and fibrillation potentials are found. At a varying number of segments below the injury level, normal MUPs reappear, but not during voluntary activation—instead they appear during spastic activation of the body part no longer in contact with the brain. The number of segments showing denervation correlated strongly to the discontinuity of the spinal cord on MRI. By preoperative use of the described approach, the exact extent of the SCI-gap can be determined, both functionally and anatomically.

The invention will in the following be illustrated by devices covering a full gap between the two ends of an injured spinal cord, but according to additional embodiments of the invention, a device can be designed to replace only an injured section of the spinal cord. Instead of cuts perpendicular to the length of the spinal cord, the cord is cut in a different plane and the device is designed to replace the missing part.

The ratio between anteroposterior and transverse diameters, $D_a/D_t$, is referred to as RAPT. The present inventors have now found that devices having combinations of transverse diameters $D_t$ in the range of around 9-13 mm, where RAPT is within the range of 0.5-1.0, and more specifically within the range of from 0.6-0.9, fulfills the need in the majority of situations with thoracic injuries, considering the spinal cord dimensions of the population. In a specific embodiment, the anteroposterior diameters $D_a$ are in the range of around 6-10 mm. The devices can roughly be divided into three groups i) Round with an RAPT value approaching 1.00, i.e. 0.8-1.0, ii) Normal with an RAPT around 0.70-0.80 and Flat with an RAPT value around 0.50-0.70. The length may vary considerably, but a series of devices having respective lengths in the range of from 15-40 mm fulfills this basic need in many situations. However, equipments for moulding spinal cord devices can easily be adjusted to a less usual, patient specific device length, if necessary. Accordingly, devices according to the present invention can be used in surgical treatment of a majority of spinal cord injuries. In particular, a kit comprising a series of preformed devices according to the invention, which are substantially evenly distributed within the dimensional ranges defined above, provides a very important tool for surgical treatment. A hospital or similar institution equipped with device kits according to the invention is well prepared for treatment of a patient having a spinal cord injury which has been identified as a candidate for this type of surgical treatment. Even if a complete traumatic spinal cord injury, in particular at the thoracic level, is a major criterion for use of a device designed for replacing a gap between two fully resected ends of the spinal cord, alternative devices can be produced for replacement of only a section of the surface area as appropriate.

Several biocompatible and/or biodegradable materials have been suggested in prior art literature for use as implants in various parts of the body, including the use for manufacture of spinal cord devices, and are suitable for use in the present devices. Examples of such materials are fibrin glue, poly-L-lactic acid (PLA) polymers, poly(lactide-co-glycolide acid (PLGA) polymers, poly-glycolic acid (PGA) polymers, polycaprolactones and calcium sulphate, just to mention a few. Important functions of the material are to provide a sufficient stable matrix for manipulation of the nerve channels and to provide the desired slow-release of medicaments of various types, to be administered at the site for surgery, in particular growth factors. Therefore, even if biodegradation is a more or less continuous process, the matrix must remain over a time sufficient for the nerve ends to grow together for sufficiently firm attachment to resist mechanical forces due to movements by the patient. For slow-release, the matrix is preferably porous so that it provides sufficient surface for adsorption/absorption of the substances to be administered.

The primary choice, at present, of material for production of spinal cord devices according to the present invention, is α-calcium sulphate hemihydrate, which has a long history of clinical use and has been demonstrated to be well tolerated with rapid and complete resorption of the degradation products, without any significant inflammatory response. Further, it has been used as vehicle for FGF, antibiotics and small molecule drugs, i.e. substances of the type that can be used also in connection with spinal cord device implantation. The invention will, in the following, be exemplified by one embodiment where α-calcium sulfate hemihydrate is used for manufacture of the device, but other materials known by a person skilled in the art can of course be used instead.

A device according to one aspect of the invention is characterized by a "cylindrical" body with more or less ellipsoidal cross section and end surfaces as indicated by the various RAPT values discussed above. The device is made of a biocompatible and biodegradable material, having nerve guiding channels which are open, as delivered, or can optionally be opened in connection with final preparation for surgery. A kit of devices according to the invention comprises a set of devices with dimensions distributed substantially evenly within the ranges defined above. With such a kit, a hospital is well equipped for handling a majority of candidates for this kind of treatment. According to a further embodiment of the invention, kits covering a more narrow range of dimensions can be provided. In one embodiment, such a narrow kit is chosen after initial pre-surgical determinations of the dimensions, while the final choice is made immediately prior to implantation, i.e., during surgery, when the final gap in the spinal cord has been created and the more exact dimensions can be measured in situ. Based on the initial pre-surgical measurements, a patient specific kit can be selected and ready for the final implantation procedure, comprising device selection, soaking in the appropriate solutions, and introduction of nerve tissue into the channels immediately before implantation.

In situations with only a partly injured and removed section of the spinal cord, the device is designed to cover a gap which is only a section (fraction) of the "cylindrical" end surface, where these sections (fractions) even may be different at the two end surfaces.

According to one embodiment for fabrication of devices according to the invention, "cylindrical" steel moulds are used. The moulds preferably have two ellipsoidal end plates separated by a distance h which corresponds to the length of the device to be produced. For creation of nerve guiding channels in the device, several through structures spanning the interior between the two ellipsoidal end plates are used during moulding. When the through structures are removed, the channels are created. The end of each channel is positioned at a specific location at each end surface for optimal contact between white and gray matter. The channels can have the same cross-section over the full length, i.e. between the two end surfaces but can also have a funnel shape in order to connect the gray and white nerve tissue as effectively as possible at the two ends. In one embodiment of the invention, the cross-section area to be connected to the white matter is larger than the cross-section area to be connected to the gray matter.

Examples of such through structures are threads, for example suture threads, or tubings which are fixed between specific positions at the mould end surfaces defined by the topography of the white and gray substances in the spinal cord.

In a specific embodiment for manufacturing a device, cylindrical steel moulds are mounted in a mould fixture with end plates of a desired ellipsoidal dimension to fit the neuroanatomical shape of a resected spinal cord. Polymer, for example, polytetrafluoroethylene (PTFE), tubings or threads are inserted between the upper end plate and the lower end plate, thereby spanning the interior of the mould and forming the channels for later positioning of the nerve grafts. α-Calcium sulphate hemihydrate powder (or other biocompatible, biodegradable material) is mixed with water for injection in suitable proportions, e.g. 1:0.30 (w/v), and injected into the mould. During setting, the mould is vibrated to remove air bubbles from the calcium sulphate paste. After around 1 h setting at room temperature, the device is released from the mould. Moulding generates a spinal cord device composed of calcium sulphate dihydrate ($CaSO_4 \times 2H_2O$) as determined by x-ray diffraction analysis. The threads or tubings are at some stage removed and channels for positioning of peripheral nerve grafts are formed. This may be done at the manufacturing step or just prior to implantation. By using tubings with different dimensions, the channels for positioning of the peripheral nerves can be adopted for optimal connection between spinal cord tracts of various dimensions and at different vertebrae levels, after implantation and nerve growth. The preformed device can be provided to the surgical team with open channels or with channels which are opened by removing the through structures (threads or tubing), e.g. by pulling the structure out of the device, as one step in the final preparation for surgery. In a specific embodiment, the devices are delivered with open channels and each of the open channels comprises a thin thread which later on can be used for pulling peripheral nerves into the channel. The device is easily equipped with such threads when the through structure is removed. Other ways for inserting peripheral nerves into the channels are also available, e.g. by suction.

It is known that growth factors, e.g. FGF1, play an important role in nerve regeneration and nerve healing and one or more growth factors, as well as other pharmaceutically active components are optionally administered to the site of implantation of a spinal cord device according to the invention. Such administration can be made in many different ways, e.g. by providing the components adsorbed or absorbed to the device. In particular, with porous or at least partly porous devices, a sufficient surface area is available for binding the component(s). According to one embodiment of the invention, the device prior to implantation is contacted with an aqueous solution comprising the component or a cocktail of components, e.g. by soaking the device in the solution for a given time period, e.g. 10-50 ml.

Such a standard solution may comprise one or more components selected from the following groups of substances: FGF1, Brain derived neurotrophic factor (BDNF), Glial derived neurotrophic factor (GDNF), neurotrophic factor (NGF), ciliary neutrophic factor (CNTF), Chondroitinase ABC, Calcium flow antagonists increasing the regeneration, e.g. nimodipine, peptidases, S-mRNA, autologous activated macrophages, macrophages from donors, olfactory ensheating cells, autologous stem cells, oligodendrocyte progenitors, Schwann cells, Cortisone, angiogenesis inhibitors, erytropoetin, inactivators of Rho (e.g. Cethrin), broad spectrum antibiotics (e.g. Minocycline), Riluzole and physiological antagonists to the NMDA-receptor, e.g magnesium. Several additional components may be of importance, e.g. pre-degenerated peripheral nerve grafts, EGF, NT-3, PDGF, IGF1, Insulin, bFGF, HGF, Calpain inhibitor, Hematopoetic inhibitor, Induced pluripotent stem cells, Neuronal stem cells, Embryonic stem cells, Mesenchymal stem cells, Anti Nogo, Rho antagonist, PEG and/or EPO.

For loading the device with an effective amount of FGF1, for example, the device is soaked in a solution comprising about 0.005-50 microgram/ml of FGF1 for about 0.5-5 hours. In one example, the concentration of the solution is 0.5 microgram/ml and the device is soaked for 1 hour in 30 ml solution. In additional embodiments, for even better effect of FGF1, the FGF1 is mixed with heparin which binds and activates FGF1, e.g. at a molar ratio of around 1:100. A suitable dose of the heparin-activated FGF1 to be delivered by the device is in the range of 0.01-100 ng/mg device, more specifically, 0.1-10 ng/mg device, or more specifically, 0.5-5 ng/mg device, and in particular around 1 ng/mg device. After implantation, the device will deliver the active component(s) over a few weeks, with the main amount being delivered over a few days.

Prior to implantation, peripheral nerves are positioned in the open channels of the device. This can be done by pulling a nerve into each of the channels. The nerve can be an autologous peripheral nerve (taken from the patient), but can also be artificial nerve tissue produced by nerve cell culturing, preferably of nerve cells taken from the patient. After loading the device with a standard solution of pharmaceutically active components or a cocktail designed for a specific patient, nerve tissue is applied in each of the channels and the device is ready for implantation.

For creating descending motor pathways from cranial (proximal) white matter to caudal (distal) gray matter over the gap between the two ends of the spinal cord and ascending sensory pathways from caudal (distal) white matter to cranial (proximal) gray matter, the device is equipped with several through channels. In order to obtain an appropriate combination of pathways in the two directions, at least some of the channels are allowed to be non-linear. In one embodiment, the device has a first set of channels having a first diameter and a second set of channels having a second diameter, where the first diameter is larger than the second diameter, as illustrated by channels A, B, C, D, E and F in FIG. 2. In one embodiment, the channels A have a first diameter in the range of from 2.0-2.9 mm, and one or more of channels B, C, D, E and F have a second diameter in the range of from 1.1-1.6 mm. In one embodiment, each channel of the first diameter has a cross section area of from about 3-7 mm$^2$ and each channel of the second diameter has a cross section area of 0.8-2.0 mm$^2$.

Figure 2:
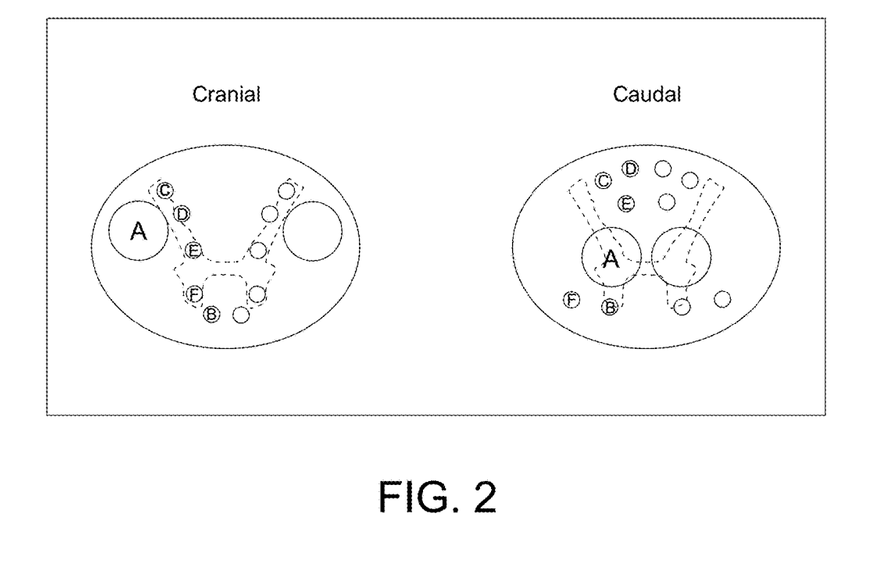
FIG. 2 shows a schematic cross section of the end surfaces of a spinal cord device with open channels of at least two different two diameters for insertion of nerve tissue.
Figure 3:
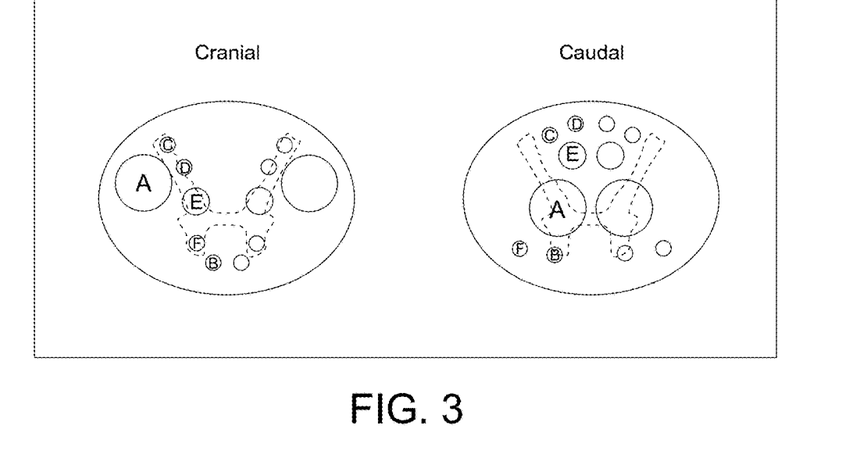
FIG. 3 shows a schematic cross section of the end surfaces of a spinal cord device with open channels of three diameters for insertion of nerve tissue superimposed on the spinal cord cross section. Channels A and B represent channel cross-section areas of descending motor tracts. Channels C, D, E and F represent cross-section areas of ascending sensory tracts. The device diameter is approximately 1 mm larger than the spinal cord diameter it aims to fit.
Figure 4:
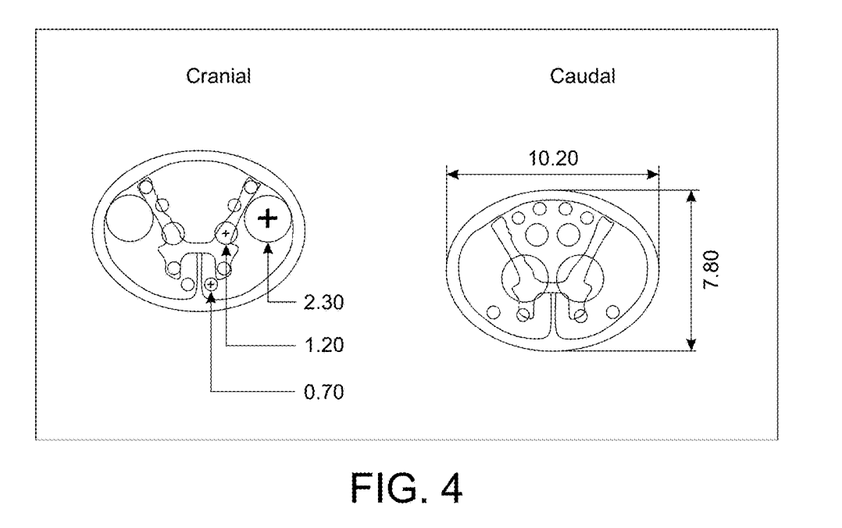
FIG. 4 shows a schematic cross section of one specific embodiment of a device according to the invention.
Figure 5:
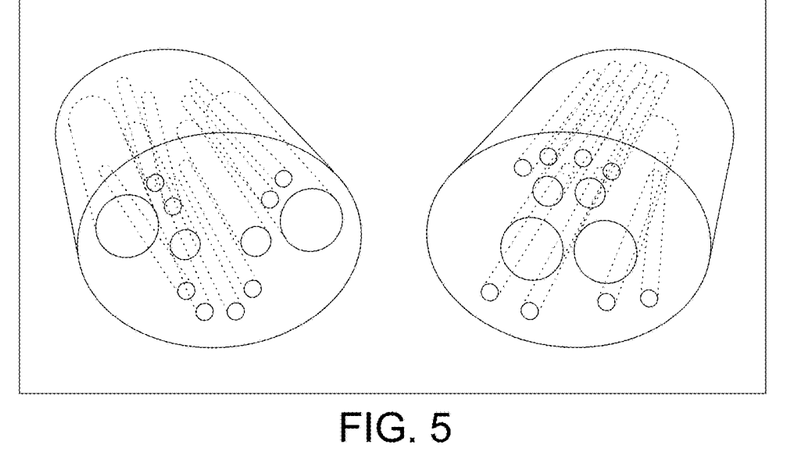
FIG. 5 shows perspective views of the channels through the device body (10) between the cranial end surface (11) and the caudal end surface (12) of the device.

In further embodiments, the spinal cord device according to the invention comprises channels A, B, C, D, E and F positioned as shown in FIG. 2, or comprises channels A, B, C, D, E and F positioned as shown in FIGS. 3 and 5. In a further embodiment, the spinal cord device according to the invention comprises channels A, B, C, D, E and F positioned and relatively sized as shown in FIGS. 3 and 5. In a specific embodiment as shown in FIG. 3, the device comprises a third set of channels (B, C, D and F) having a shorter diameter than the first set of channels (A) and the second set of channels (E). In a more specific embodiment, the channels A have a first diameter in the range of from 2.0-2.9 mm, the channels E have a second diameter in the range of from 1.1-1.6 mm, and the channels B, C, D and F have a third diameter of 0.5-0.9 mm. In further embodiments, channels A of the first diameter have a cross section area of from about 3-7 mm$^2$, channels E of the second diameter have a cross section area of 0.8-2.0 mm$^2$, and channels B, C, D and F of the third diameter have a cross section area of 0.2-0.7 mm$^2$. A more specific embodiment is shown in FIG. 4. One or more additional sets of channels may be introduced in further embodiments. In all figures, only the channels on the left side of the symmetry plane are marked but the designations given are relevant also for the corresponding channels on the right side.

The position and diameter of the through channels in each of the end surfaces of the device is of importance in order to obtain the best conditions for guidance of the important longitudinal tracts over the spinal cord gap. The inventors have found that, in accordance with one embodiment of the invention, these conditions can be obtained by about 12 channels, and in further embodiments the channels are positioned as illustrated in FIG. 2 or as illustrated in FIG. 3.

It is desirable to use as much surface area as possible in the spinal cord tract channels, but at the same time, the wall of each channel needs to be thick enough so as not to be crushed during manufacture and manipulations prior to implantation. The requirement in this respect may vary depending on the material used and the manufacturing method. The inventors have found that a preferred wall thickness, in particular with the α-calcium sulphate hemihydrate used in the embodiment illustrating the invention, is around 0.3 mm or somewhat higher. Channels A have a diameter in the range of 2.0-2.9 mm, channels B, C, D and F have a diameter in the range of 0.6-0.9 mm and channels E have a diameter in the range of 1.1-1.6 mm. The position in each surface of the channels is illustrated in FIGS. 2 and 3 according to specific embodiments of the invention.

Preferably, channels creating the descending motor pathway from white matter on the cranial (proximal) side to gray matter on the caudal (distal) side, have a substantially 100% connection to the white matter on the proximal side, "the motor channel entrance". On the caudal (distal) motor exit side, the percentage of the channel surface that connects to gray matter is more than 50%, e.g. in the interval 50-60%, or preferably 50-70%. According to one embodiment where the funnel type of channels discussed above are used, an even higher percentage can be achieved, e.g. higher than 60%, 70%, 80% or 90%.

Channels creating the ascending sensory pathway from white matter on the caudal (distal) side to gray matter on the cranial (proximal) side preferably have substantially 100% connection to the white matter on the distal side. At least 60%, e.g. in the interval 60-80% of the channel openings connects gray matter on the proximal side. This percentage can be increased in embodiments with suitable modification of the channel dimensions, in particular funnel shaped channels.

By using the functional tracts of the white matter, it has been found that with the present design of the channel system it is possible to obtain good function even if the total area of white matter on the cranial (proximal) side connected to motor descending channels is low. This percentage of covered white matter is greater than 10%, and in particular greater than 15%, e.g. covering an interval of 15-30% in one embodiment of the invention.

The corresponding percentage of channel areas connected to ascending sensory white matter on the caudal (distal) side is at least 5%, preferably greater than 10%, e.g. in the interval 10-20% in one embodiment of the invention.

According to one embodiment of the invention, kits are provided comprising a number of devices covering a desired number of alternative dimensions. One example of such a kit comprises around 10 devices with different end surface dimensions and configurations, i.e., designs, and will cover the major number of cross-section alternatives in the thoracic example. In an additional embodiment, for each of these end surface configurations or designs, devices with different lengths are produced. In one embodiment, at least two devices are provided having the same $D_t$, $D_a$, RAPT and Channel Diameter dimensions and differing lengths L. In another embodiment, for each configuration or design, at least two devices are provided having differing lengths L. In another embodiment, devices of 6 different lengths are provided for each surface configuration or design, whereby an example of such a kit having ten different end surface designs contains 60 devices. Again, it should be stressed that this is only one example of a device kit according to the invention.

An example of cross-sectional areas and channel diameters of a kit comprising devices according to the invention, fulfilling a hospital's basic need for devices for selection in preparation for implantation in a thoracic injury situation is given below. Each of these device designs is provided with various lengths, e.g. in the 15-40 mm range. With 6 lengths for each, evenly distributed within the range, a typical kit comprises in total around 60 devices (dimensions given in mm):

| Design No. | $D_t$ | $D_a$ | RAPT | Channel Diameter A | E | B, C, D, F |
|---|---|---|---|---|---|---|
| 1 | 9.25 | 7.83 | 0.85 | 2.00 | 1.10 | 0.60 |
| 2 | 10.40 | 8.78 | 0.84 | 2.30 | 1.20 | 0.70 |
| 3 | 11.56 | 9.74 | 0.84 | 2.60 | 1.40 | 0.80 |
| 4 | 9.00 | 6.92 | 0.77 | 2.00 | 1.10 | 0.60 |
| 5 | 10.20 | 7.80 | 0.76 | 2.30 | 1.20 | 0.70 |
| 6 | 11.40 | 8.69 | 0.76 | 2.60 | 1.40 | 0.80 |
| 7 | 12.60 | 9.57 | 0.76 | 2.90 | 1.60 | 0.90 |
| 8 | 9.83 | 6.61 | 0.67 | 2.00 | 1.10 | 0.60 |
| 9 | 11.18 | 7.53 | 0.67 | 2.30 | 1.20 | 0.70 |
| 10 | 12.58 | 8.45 | 0.67 | 2.60 | 1.40 | 0.80 |

In this example, the kit comprises 10 devices with different surface area dimensions and configurations, i.e., designs. However, the number of devices in a kit can of course be different depending on the ambition to cover gaps with different configurations.

After diagnosis, based on MRI results, which gives a rough estimate of the anteriposterior and transversal dimensions of the spinal cord injury to be a candidate for spinal cord implantation, the spinal cord ends are resected as necessary. The surface dimensions, i.e. $D_t$ and $D_a$, and the length L of the gap between the two spinal cord ends, are determined. This can be done in many different ways and a series of dummies with a wide range of dimensions ($D_t$, $D_a$ and L) are preferably used in situ for this determination. A device with the same shape, but approximately 1 mm larger diameter, is selected.

The device is contacted with the solution comprising one or more pharmaceutically active component(s) to be administered to the site of surgery, e.g. heparin-activated FGF1. In the next step nerve tissue is introduced into all channels in the device, and the device is then implanted.

EXAMPLES

Example 1

This example evaluates a biodegradable calcium sulphate device with heparin-activated rhFGF1 for treatment of spinal cord injury in rat.

SCI devices fabricated from α-calcium sulfate hemihydrate with 12 channels with similar geometry as shown in FIG. 5 were loaded with heparin-activated rhFGF1. The test animals, Sprague Dawley rats, were allocated into 5 study groups. Laminectomy was carried out on all animals independent of study group. The spinal cord of the control groups were either transected (group 1, negative control) or left intact (group 2, positive control). The spinal cords of the rats of groups 3-5 were transected and the removed spinal cord tissue was replaced by devices containing nerve grafts. The SCI-devices employed for study group 4 were soaked in 500 μg/ml heparin-activated rhFGF1 (rhFGF1:heparin, 1:1, w/w). For study group 5 the SCI-devices were soaked in 50 μg/ml heparin-activated rhFGF1. Due to autophagy, a few animals had to be sacrificed prior to the end of the 20 week study. The animals sacrificed before week 20 were evenly spread among the groups.

Before sacrifice, motor evoked potentials (MEPs) were measured in the hind limbs of the rats. The motor function of the rats was evaluated weekly during the in-life period of the study. All animals treated with the SCI-device, soaked in 500 or 50 μg/ml heparin-activated rhFGF1 (groups 4 and 5) showed positive MEP scores in both hindlimbs at 20 weeks (range 17-23) weeks) post surgery. Animals with spinal cord resection only did not demonstrate any bilateral positive MEP signals. To verify that the signal was mediated by regenerated axons, the spinal cord was re-lesioned and a second measurement was performed. None of the re-lesioned animals exhibited positive MEPs.

Example 2

This example evaluates dose-finding of heparin-activated rhFGF1 administered in a biodegradable calcium sulphate device for treatment of spinal cord injury in rat.

The same type of devices as in Example 1 were used. Each device was soaked in heparin-activated rhFGF1 (FGF1:heparin, 1:100 molar ratio) solution for 1 h at room temperature. Heparin solution without preservatives (10000 IE/ml $H_2O$, Leo Pharma Denmark) was employed. The devices were soaked in 50 µg/ml, 0.5 µg/ml, 0.005 µg/ml and 0 µg/ml concentrations of heparin-activated rhFGF1 corresponding to a dose of 45, 0.9, 0.01 and 0 ng/mg device (based on solution uptake and adsorption).

Figure 6:
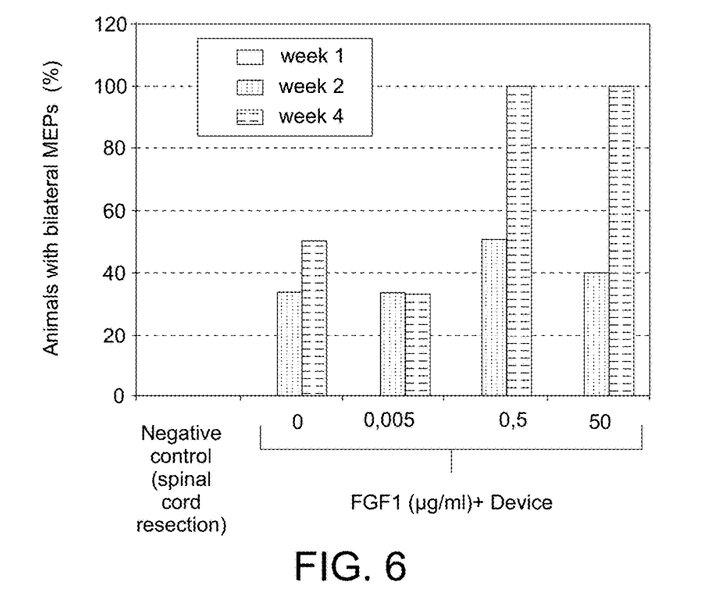
FIG. 6 illustrates FGF1-dependent recovery of bilateral MEPs in the hindlimbs of treated animals as described in Example 2.

FGF1-dependent recovery of bilateral MEPs in the hindlimbs of treated animals is illustrated in FIG. 6. All animals showed undetectable MEPs in the hindlimbs 1 week post-surgery, while already after 2 weeks positive MEPs were recorded. The results indicate that an effective dose of heparin-activated rhFGF1 in the disclosed device in the treatment of complete SCI in rat is achieved with a concentration of at least 0.5 µg/ml heparin-activated rhFGF1 solution (yielding 0.9 ng heparin-activated rhFGF1/mg device).

Example 3

Implantation of Heparin-Activated rhFGF1 Loaded SCI-Devices with Peripheral Nerve Grafts in Pig—Development of Operation Technique and Limited Safety Study Clinical SCI-devices as illustrated in FIG. 5, 15 mm high and having an oval cross section of 9.0-6.9 mm, comprising 12 channels for nerve graft positioning are made from α-calcium sulphate hemihydrate with subsequent sterilization.

Each device is placed in 30 ml of a soaking solution consisting of 5 µg/ml rhFGF1, 80 µg/ml Gentamicin, 10 mM $NaPO_4$, 150 mM NaCl, 0.3 mM EDTA at pH 7 for 1 hour to allow the solution to be adsorbed into the device. The heparin concentration is 430 µg/ml and the ratio rhFGF1:heparin 1:100 (molar).

The animals are female Landrace pig. After 10 days of acclimatization, the pig is anaesthetized with a combination of fentanyl, midazolam and propofol and prepared for surgery. During the surgical procedure, the intravenous anaesthesia is maintained with fentanyl 0.004 mg/kg/h, midazolam 0.5 mg/kg/h and propofol 3 mg/kg/h. The preparation for surgery comprises disinfection of the areas subjected to surgery, combined with antibiotic treatment.

An incision is made above the large vessels in the neck and the vascular sheat is explored. A central venous catheter is inserted and secured in the jugular vein for infusion of fluids and administration of intensive care medications if necessary.

The pig is placed with the back up. An incision is made above the thoracic spinal cord and a laminectomy is performed. The dura mater is incised and the spinal cord is exposed. A segment large enough to fit the SCI device of the lower thoracic spinal cord is resected.

An incision is made in the lower hind limb where after nerves, suitable for the SCI device are exposed and resected. The nerves are trimmed into adequate dimensions for insertion in the SCI device, which has been soaked in the rhFGF1 solution for one hour. Subsequently, the peripheral nerves are pulled through the 12 channels in the device. The nerve endings are trimmed at the device surface and the device is inserted into the spinal cord gap in such a way that the indicator on the device is dorsal and cranial. Subsequently, the SCI-device is attached to the spinal cord stumps. The dura mater is closed as well as muscle layers and skin.

Within the five days available for observation the device is partly adhered to spinal cord.

The specific embodiments and examples set forth in the present specification are illustrative in nature and are not limiting of the scope of the invention defined by the present claims. Although various aspects of the disclosed devices, kits and methods may occur to those skilled in the art upon reading the specification, the present invention includes such modifications and is limited only by the scope of the claims.

What is claimed is:

1. A method for restoring or at least substantially restoring an injured spinal cord of a patient, comprising the steps of
    i) determining the cross-section surface area and the anteroposterior diameter ($D_a$)/transverse diameter ($D_t$) ratio (RAPT) of an injured section of the spinal cord after resection of the nerve ends as necessary to reach healthy spinal cord tissue,
    ii) selecting a spinal cord device having the ratio anteroposterior/transverse diameter (RAPT) determined in i), a slightly larger surface area than the spinal cord cross-section surface area to fit the dimensions of said injured section for optimal connection between the spinal cord tracts, and through channels with openings in a cranial surface and a caudal surface of the spinal cord device,
    iii) positioning peripheral autologous nerves in the through channels, and
    iv) implanting the device to bridge the gap in the injured spinal cord.

2. The method according to claim 1, wherein the device is soaked in a solution comprising FGF1 before implantation.

3. The method according to claim 1, wherein the i-s device is soaked in a solution comprising one or more pharmaceutically active substances before implantation.

4. A method for restoring or at least substantially restoring an injured spinal cord of a patient, comprising the steps of
    i) determining the cross-section surface area and the anteroposterior diameter ($D_a$)/transverse diameter ($D_t$) ratio (RAPT) of an injured section of the spinal cord after resection of the nerve ends as necessary to reach healthy spinal cord tissue,
    ii) selecting a spinal cord device comprising a body formed of a biocompatible, biodegradable matrix, the body including a proximal, cranial surface and a distal, caudal surface for connection to two ends of an injured spinal cord after removal of an injured spinal cord section, the body having through channels with openings in the cranial surface and the caudal surface for connection of descending motor pathways from cranial white to caudal gray matter and ascending sensory pathways from caudal white to cranial gray matter of the two spinal cord ends, the spinal cord device having a transversal diameter ($D_t$), an anteroposterior diameter ($D_a$) and a length (L), wherein $D_t$ is within a range of from 9 to 13 mm and the ratio anteroposterior diameter/ transverse diameter (RAPT) is in a range of from 0.5 to 1.0, and wherein the position and dimension of the channels, the RAPT value, and the cranial surface area and/or the caudal surface area of the device are adopted to the shape, level, dimension of white and gray matter, and size of the injured spinal cord for optimal connection between spinal cord tracts having the ratio antero-posterior/transverse diameter (RAPT) determined in i) and a slightly larger surface area than the spinal cord cross-section surface area to fit the dimensions of said injured section for optimal connection between the spinal cord tracts, iii) positioning peripheral autologous nerves in the through channels, and iv) implanting the device to bridge the gap in the injured spinal cord.

5. The method according to claim 4, wherein the device is soaked in a solution comprising FGF1 before implantation.

6. The method according to claim 4, wherein the i-s device is soaked in a solution comprising one or more pharmaceutically active substances before implantation.

7. The method according to claim 1, wherein the spinal cord device comprises a body formed of a biocompatible, biodegradable matrix, the body including a proximal, cranial surface adapted for implantation on a cranial end of an injured spinal cord and a distal, caudal surface adapted for implantation on a caudal end of an injured spinal cord, for connection to a cranial end and a caudal end, respectively, of an injured spinal cord after removal of an injured spinal cord section; the body having two sets of through channels A, B, C, D, E and F with openings in the cranial surface and the caudal surface for connection of descending motor pathways from cranial white to caudal gray matter and ascending sensory pathways from caudal white to cranial gray matter of the two spinal cord ends; the spinal cord device having a length (L), a $D_t$ within a range of from 9 to 13 mm and a RAPT in a range of from 0.5 to 1.0;

wherein
(a) the two sets of channels A-F are symmetrically arranged in each of the cranial surface and the caudal surface of the implant at locations corresponding with anatomical positions in the cranial end and caudal end, respectively, of the removed spinal cord section, (b)(i) in the cranial surface:
the channels A are positioned in opposite lateral funiculi and adjacent opposite posterior horns,
the channels B are positioned in opposite anterior funiculi and adjacent the ends of opposite anterior horns,
the channels C are positioned in gray matter at the ends of opposite posterior horns,
the channels D are positioned in the posterior horns, between channels C and the lateral horns,
the channels E are positioned in the posterior horns, between the channels D and the lateral horns, and
the channels F are positioned in the anterior horns, between the channels B and the lateral horns, and (b)(ii) in the caudal surface:
the channels A are positioned at the juncture of the respective anterior horn, posterior horn and the intermediate gray,
the channels B are positioned in gray matter at the ends of opposite anterior horns and in opposite anterior funiculi adjacent the ends of the respective anterior horns,
the channels C are positioned in opposite posterior funiculi and between the ends of opposite posterior horns,
the channels D are positioned in opposite posterior funiculi and between the opposite channels C,
the channels E are positioned in opposite posterior funiculi and between the openings for channels D and the intermediate gray matter, and
the channels F are positioned in opposite lateral funiculi and adjacent the respective anterior funiculi, and (c)(i) channels A have a first diameter in a range of from 2.0-2.9 mm, and one or more of channels B, C, D, E and F have a second diameter in a range of from 1.1-1.6 mm, or (c)(ii) channels A have a first diameter in a range of from 2.0-2.9 mm, channels E have a second diameter in a range of from 1.1-1.6 mm, and channels B, C, D and F have a third diameter in a range of from 0.5-0.9 mm.

* * * * *

UNITED STATES PATENT AND TRADEMARK OFFICE
CERTIFICATE OF CORRECTION

PATENT NO. : 9,895,234 B2
APPLICATION NO. : 14/361650
DATED : February 20, 2018
INVENTOR(S) : Arvid Frostell et al.

It is certified that error appears in the above-identified patent and that said Letters Patent is hereby corrected as shown below:

Claim 3, Column 12, Line 44, delete "i-s".

Claim 6, Column 13, Line 20, delete "i-s".

Signed and Sealed this
Twenty-second Day of May, 2018

Andrei Iancu
*Director of the United States Patent and Trademark Office*